US010464874B2

(12) United States Patent
Friedrich et al.

(10) Patent No.: US 10,464,874 B2
(45) Date of Patent: Nov. 5, 2019

(54) FLUORINATED TENSIDES

(71) Applicant: Merck Patent GmbH, Darmstadt (DE)

(72) Inventors: Reiner Friedrich, Seeheim-Jugenheim (DE); Julian Osthoff, Dieburg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/120,288

(22) PCT Filed: Feb. 18, 2015

(86) PCT No.: PCT/EP2015/000352
§ 371 (c)(1),
(2) Date: Aug. 19, 2016

(87) PCT Pub. No.: WO2015/124290
PCT Pub. Date: Aug. 27, 2015

(65) Prior Publication Data
US 2017/0121260 A1    May 4, 2017

(30) Foreign Application Priority Data
Feb. 21, 2014   (EP) ..................... 14000616

(51) Int. Cl.
| C07C 43/12 | (2006.01) |
| C07C 217/28 | (2006.01) |
| C07C 229/12 | (2006.01) |
| C07C 309/10 | (2006.01) |
| C07C 59/135 | (2006.01) |
| C07C 69/708 | (2006.01) |

(52) U.S. Cl.
CPC .......... C07C 43/126 (2013.01); C07C 59/135 (2013.01); C07C 69/708 (2013.01); C07C 217/28 (2013.01); C07C 229/12 (2013.01); C07C 309/10 (2013.01)

(58) Field of Classification Search
CPC ... C07C 43/126; C07C 59/135; C07C 69/708; C07C 217/28; C07C 229/12
See application file for complete search history.

(56) References Cited

U.S. PATENT DOCUMENTS

| 4,292,402 A | 9/1981 | Pollet |
| 4,968,599 A | 11/1990 | Pitt et al. |
| 4,988,610 A | 1/1991 | Pitt et al. |
| 6,890,608 B2 | 5/2005 | Morishima et al. |
| 7,635,789 B2 | 12/2009 | Foo |
| 7,691,282 B2 | 4/2010 | Flynn et al. |
| 7,737,307 B2 | 6/2010 | Murphy et al. |
| 7,777,075 B2 | 8/2010 | Ishikawa |
| 8,071,816 B2 | 12/2011 | Flynn et al. |
| 9,416,085 B2 | 8/2016 | Marchionni |
| 9,938,306 B2 | 4/2018 | Qiu et al. |
| 9,938,307 B2 * | 4/2018 | Qiu ..................... C09D 183/08 |
| 2003/0153780 A1 | 8/2003 | Haniff et al. |
| 2005/0107645 A1 | 5/2005 | Furukawa |
| 2005/0127322 A1* | 6/2005 | Costello ............... C07C 43/126 252/71 |
| 2007/0051916 A1 | 3/2007 | Flynn et al. |
| 2008/0093582 A1 | 4/2008 | Nagai et al. |
| 2008/0149878 A1 | 6/2008 | Kirsch et al. |
| 2009/0043133 A1 | 2/2009 | Murphy et al. |
| 2009/0326083 A1 | 12/2009 | Flynn et al. |
| 2010/0003737 A1 | 1/2010 | Murphy et al. |
| 2011/0088594 A1 | 4/2011 | Claus et al. |
| 2011/0118428 A1 | 5/2011 | Hierse et al. |
| 2012/0111233 A1 | 5/2012 | Hierse et al. |
| 2012/0277460 A1 | 11/2012 | Percec et al. |
| 2012/0329976 A1 | 12/2012 | Drysdale et al. |
| 2013/0269568 A1 | 10/2013 | Claus et al. |

FOREIGN PATENT DOCUMENTS

| CN | 1665768 A | 9/2005 | |
| CN | 101772567 A | 7/2010 | |
| EP | 1522536 A1 | 4/2005 | |
| JP | S55-116799 A | 9/1980 | |
| JP | 09-111286 A | 4/1997 | |
| JP | 2001-133984 A | 5/2001 | |
| JP | 2004-18394 A | 1/2004 | |
| JP | 2007-238583 A | 9/2007 | |
| JP | 2009-167184 A | 7/2009 | |
| JP | 2011-527308 A | 10/2011 | |
| JP | 4822265 B2 * | 11/2011 | ............. C07C 43/12 |
| WO | 03/010128 A2 | 2/2003 | |
| WO | 2004002932 A1 | 1/2004 | |
| WO | 2006/072401 A1 | 7/2006 | |
| WO | 2009/020907 A1 | 2/2009 | |
| WO | 2009/149807 A1 | 12/2009 | |
| WO | 2010/002623 A2 | 1/2010 | |
| WO | 2010/003567 A2 | 1/2010 | |

(Continued)

OTHER PUBLICATIONS

Matsukawa et al. "Preparation of fluorine-containing polyethers." JP 4822265 B2 (Nov. 24, 2011) English machine translation. (Year: 2011).*

Chi et al. "A facile synthesis of partly-fluorinated ethers using perfluoropropoxyethylene and aliphatic alcohols." Bull. Kor. Chem. Soc. 1999, 20, 220-222. (Year: 1999).*

Chemical Abstract Service, STN Registry Database [online], Registry No. 1112274-65-3 [Entered STN: Feb. 26, 2009]. (Year: 2009).*

Wu et al. "Complex Columnar Hexagonal Polymorphism in Supramolecular Assemblies of a Semifluorinated Electron-Accepting Naphthalene Bisinnide" J. Am. Chem. Soc. 2015, 137, 807-819 (pub. Dec. 30, 2014). (Year: 2014).*

(Continued)

*Primary Examiner* — Amanda L Aguirre
(74) *Attorney, Agent, or Firm* — Millen White Zelano and Branigan, PC; Csaba Henter

(57) ABSTRACT

The present invention relates to novel compounds containing fluorinated end groups, to the use thereof as surface-active substances, and to compositions comprising these compounds.

22 Claims, No Drawings

(56) References Cited

FOREIGN PATENT DOCUMENTS

| WO | 2010/149262 | A1 | | 12/2010 | |
|---|---|---|---|---|---|
| WO | 2011/082770 | A2 | | 7/2011 | |
| WO | 2012/084118 | A1 | | 6/2012 | |
| WO | WO-2016032738 | A1 | * | 3/2016 | ............ C07F 7/1836 |

OTHER PUBLICATIONS

International Search Report dated May 6, 2015 issued in corresponding PCT/EP2015/000352 application (3 pages).

Z.T. Liu et al., "Phase Behaviors of Aerosol-OT Analogue Fluorinated Surfactants in 1,1,1,2-Tetrafluoroethane and Supercritical $CO_2$", Ind. Eng. Chem. Res., vol. 46, No. 1 (2007) pp. 22-28.

A.R. Pitt, "The Efficiency of Dynamic Surface Tension Reductions Within Homologous Series of Surfactants in Aqueous Gelatin Solution", Progr. Colloid Polym. Sci., vol. 103 (1997) pp. 307-317.

A.R. Pitt et al., "The Relationship Between Surfactant Structure and Limiting Values of Surface Tension, In Aqueous Gelatin Solution, With Particular Regard to Multilayer Coating", Colloids and Surfaces A: Physiochemical and Engineering Aspects, vol. 114 (1996) pp. 321-335.

G.L. Kennedy et al., "The Toxicology of Perfluorooctanoate", Critical Reviews in Toxicology, vol. 34, No. 4 (2004) pp. 351-384.

English Abstract of JP 2001-133984 A published May 18, 2001 (1 page).

English Abstract of JP 2004-018394 A published Jan. 22, 2004 (2 pages).

English Abstract of JP 2007-238583 A published Sep. 20, 2007 (2 pages).

Chinese Office Action dated Oct. 11, 2017 issued in corresponding CN 201580009150.1 application (9 pages).

English Abstract of EP 1522536 A1 which corresponds to CN 1665768 A published Sep. 7, 2005.

Search report in corresponding JP application No. 2016-553497 dispatched Oct. 12, 2018 (pp. 1-2).

* cited by examiner

FLUORINATED TENSIDES

The present invention relates to novel compounds containing fluorinated end groups, to the use thereof as surface-active substances, and to compositions comprising these compounds.

Fluorine-containing surfactants have unique applicational properties owing to their special surface activity. Fluorosurfactants, whose static surface tension is very low (16-20 mN/m), can be employed in a very wide variety of applications and contribute, for example, to improved wetting of surfaces. Thus, they are used, for example, as interface promoters or emulsifiers or viscosity reducers in paints, coatings or adhesives.

Classical fluorosurfactants are built up from long-chain, perfluorinated alkyl chains (C6-C8) and are regarded as potentially bioaccumulative and toxic. In general, however, fluorosurfactants contain perfluoroalkyl substituents, which are broken down in the environment by biological and other oxidation processes to give perfluoroalkanecarboxylic acids and -sulfonic acids. These are regarded as persistent and are in some cases suspected of causing health damage (G. L. Kennedy, Jr., J. L. Butenhoff, G. W. Olsen, J. C. O'Connor, A. M. Seacat, R. G. Perkins, L. B. Biegel, S. R. Murphy, D. G. Farrar, *Critical Reviews in Toxicology* 2004, 34, 351-384). In addition, longer-chain perfluoroalkanecarboxylic acids and -sulfonic acids accumulate in the food chain. Shorter-chain fluorinated building blocks are more favourable with respect to their ecotoxicological profile, but often exhibit worse properties in their areas of application.

WO 03/010128 describes perfluoroalkyl-substituted amines, acids, amino acids and thioether acids which contain a $C_{3-20}$-perfluoroalkyl group. JP-A-2001/133984 discloses surface-active compounds containing perfluoro-alkoxy chains which are suitable for use in antireflection coatings. JP-A-09/111286 discloses the use of perfluoropolyether surfactants in emulsions.

WO 2006/072401 and WO 2010/003567 describe surface-active compounds containing trifluoromethoxy groups. Compounds containing specific fluoroalkyl groups are described in U.S. Pat. No. 7,635,789, US 2008/0093582, JP 2004-18394 and WO 2010/002623. Partially fluorinated compounds are described in U.S. Pat. No. 7,737,307, EP 1 522 536 and WO 2010/002622.

Specific applications of sulfosuccinates and/or sulfotricarballylates containing various fluorinated side chains are described in U.S. Pat. Nos. 4,968,599 and 4,988,610 as well as 6,890,608 and in A. R. Pitt et al., Colloids and Surfaces A: Physicochemical and Engineering Aspects, 1996, 114, 321-335; A. R. Pitt, Progr. Colloid Polym. Sci, 1997, 103, 307-317 and Z.-T. Liu et al., Ind. Eng. Chem. Res. 2007, 46, 22-28. Further fluorosurfactants, in particular succinates and tricarballylates containing fluorinated alkyl groups, are described in WO 2009/149807, WO 2010/003567, WO 2010/149262, WO 2011/082770 and WO 2012/084118.

Furthermore, there is a demand for alternative surface-active substances which preferably do not break down on degradation to give long-chain persistent compounds.

Novel compounds have now been found which are suitable as surface-active substances and preferably do not have one or more of the above-mentioned disadvantages.

The present invention relates firstly to compounds of the formula (I)

$$Z_n \text{spacer} X_x \qquad (I)$$

where $Z = R_f - O_{o1} - A^1_{a1} - O_{o2} - A^2_{a2} - O_{o3} - B_b -$ n=1, 2, 3, 4, 5 or 6, preferably 2-4, in particular 2-3, $R_f$=fluorinated alkyl, linear or branched, preferably fluorinated C1-C6-alkyl, particularly preferably perfluorinated C1-C4-alkyl, in particular perfluorinated C1-C3-alkyl, $A^1$ and $A^2$=independently of one another $-(CF_2)-$ or $-(CF(CF_3)-CF_2)-$ or $-(CF_2-O)-$ or $-(CF_2-CF_2)-O-$, $a_1$ and $a_2$=independently of one another 0-4, $B = -CHF-CF_2-Y-(CF_2)_m-$ Y=O or S, preferably O, b=1, m=0 or 1, spacer=a saturated or unsaturated, branched or unbranched hydrocarbon unit, optionally containing heteroatoms, X is a hydrophilic group, x=1, 2, 3 or 4, preferably 1, o1, o2 and o3=independently of one another 0 or 1, where all indices are selected so that no $-O-O-$ bonds are present.

If $X = -OH$, $-Oalkyl$, $-COOH$ or $-COOalkyl$, n is then preferably 2-4, in particular 2-3.

If $X = -SO_3H$ or $-SO_3^-$, Z is then preferably not bonded to the spacer via an $-OCO-$ bond.

The hydrocarbon units of the spacer of the compounds of the formula (I) can be aliphatic or aromatic units, optionally provided with heteroatoms. The group Z in the surface-active compounds here is preferably bonded to a saturated, branched or unbranched hydrocarbon unit, preferably to a saturated, branched or unbranched alkylene group, where one or more non-adjacent C atoms may be replaced by O or N, preferably O. Preference is given, for example, to C1-C6-alkylene groups, in particular C1-C4-alkylene groups. In a variant of the invention, the preferred heteroatom-containing hydrocarbon unit used is a polyethylene glycol or polypropylene glycol unit.

In a variant of the invention, the group Z occurs multiple times in the surface-active compound, preferably twice or three times. In another variant of the invention, the group Z occurs only once in the surface-active compound. In a variant of the invention, compounds of the formula (I) may contain different group Z.

Preference is given to compounds of the formula (I) in which n=2-3 and x=1.

Preference is given to compounds of the formula (I) in which Z is equal to:

$R_f-CHF-CF_2-Y-(CH_2)_m-$ or $R_f-O-CHF-CF_2-Y-(CH_2)_m-$ or $R_f-O-(CF_2)_{1-4}-CHF-CF_2-Y-(CH_2)_m-$ or $R_f-O-(CF_2)_{1-4}-O-CHF-CF_2-Y-(CH_2)_m-$ or $R_f-O-(CF(CF_3)-CF_2)_{1-4}-CHF-CF_2-Y-(CH_2)_m-$ or $R_f-O-(CF(CF_3)-CF_2)_{1-4}-O-CHF-CF_2-Y-(CH_2)_m-$ or $R_f-O-(CF_2-O)_{1-4}-CHF-CF_2-Y-(CH_2)_m-$ or $R_f-O-(CF_2-CF_2-O)_{1-4}-CHF-CF_2-Y-(CH_2)_m-$ or $R_f-O-(CF_2-O)_{1-4}-(CF_2-CF_2-O)_{1-4}-CHF-CF_2-Y-(CH_2)_m-$ where m=0 or 1.

Particular preference is given to compounds of the formula (I) in which Z is equal to:

$R_f-CHF-CF_2-Y-(CH_2)_m-$ or $R_f-O-CHF-CF_2-Y-(CH_2)_m-$ or $R_f-O-(CF_2)_{1-4}-CHF-CF_2-Y-(CH_2)_m-$ or $R_f-O-(CF_2)_{1-4}-O-CHF-CF_2-Y-(CH_2)_m-$.

In particular, preference is given to compounds of the formula (I) where $Z=R_f-O-CHF-CF_2-Y-(CH_2)_m-$ or $R_f-O-(CF_2)_{1-4}-O-CHF-CF_2-Y-(CH_2)_m-$.

Preference is given to compounds of the formula (I) in which Rf is equal to: $CF_3-$ or $CF_3-CF_2-$ or $CF_3-CF_2-CF_2-$.

Especial preference is given to compounds of the formula (I) in which n=2-3, x=1, the spacer is a saturated, branched or unbranched hydrocarbon unit, Rf is equal to $CF_3-$, $CF_3-CF_2-$ or $CF_3-CF_2-CF_2-$ and Z is equal to:

$R_f-CHF-CF_2-Y-(CH_2)_m-$ or
$R_f-O-CHF-CF_2-Y-(CH_2)_m-$ or
$R_f-O-(CF_2)_{1-4}-CHF-CF_2-Y-(CH_2)_m-$ or
$R_f-O-(CF_2)_{1-4}-O-CHF-CF_2-Y-(CH_2)_m-$ or
$R_f-O-(CF(CF_3)-CF_2)_{1-4}-CHF-CF_2-Y-(CH_2)_m-$ or
$R_f-O-(CF(CF_3)-CF_2)_{1-4}-O-CHF-CF_2-Y-(CH_2)_m-$ or
$R_f-O-(CF_2-O)_{1-4}-CHF-CF_2-Y-(CH_2)_m-$ or
$R_f-O-(CF_2-CF_2-O)_{1-4}-CHF-CF_2-Y-(CH_2)_m-$ or
$R_f-O-(CF_2-O)_{1-4}-(CF_2-CF_2-O)_{1-4}-CHF-CF_2-Y-(CH_2)_m-$ where m=0 or 1. Particular preference is given here to compounds in which Z is equal to:

$R_f-CHF-CF_2-Y-(CH_2)_m-$ or
$R_f-O-CHF-CF_2-Y-(CH_2)_m-$ or
$R_f-O-(CF_2)_{1-4}-CHF-CF_2-Y-(CH_2)_m-$ or
$R_f-O-(CF_2)_{1-4}-O-CHF-CF_2-Y-(CH_2)_m-$, especially compounds where $Z=R_f-O-CHF-CF_2-Y-(CH_2)_m-$ or $R_f-O-(CF_2)_{1-4}-O-CHF-CF_2-Y-(CH_2)_m-$.

Particular preference is given to compounds in which the said variables, in particular all variables, have the preferred meanings, in particular the particularly preferred meanings.

In the compounds according to the invention, X is a hydrophilic group, preferably an anionic, cationic, nonionic or amphoteric group.

A preferred anionic group X can be selected from $-COO^-$, $-SO_3^-$, $-OSO_3^-$, $-PO_3^{2-}$, $-OPO_3^{2-}$, $-(OCH_2CH_2)_s-O-(CH_2)_t-COO^-$, $-(OCH_2CH_2)_s-O-(CH_2)_t-SO_3^-$, $-(OCH_2CH_2)_s-O-(CH_2)_t-OSO_3^-$, $-(OCH_2CH_2)_s-O-(CH_2)_t-PO_3^{2-}$, $-(OCH_2CH_2)_s-O-(CH_2)_t-OPO_3^{2-}$ or from the formulae A to C,

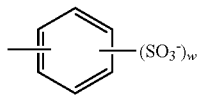

A

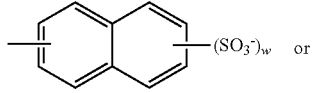

B

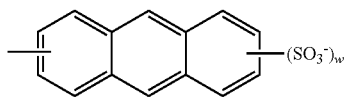

C where s stands for an integer from the range from 1 to 1,000, t stands for an integer selected from 1, 2, 3 or 4 and w stands for an integer selected from 1, 2 or 3.

The preferred anionic groups here include, in particular, $-COO^-$, $-SO_3^-$, $-OSO_3^-$, $-PO_3^{2-}$, $-OPO_3^{2-}$, the subformula A, and $-(OCH_2CH_2)_s-O-(CH_2)_t-COO^-$, $-(OCH_2CH_2)_s-O-(CH_2)_t-SO_3^-$ and $-(OCH_2CH_2)_s-O-(CH_2)_t-OSO_3^-$, where each one of these groups per se may be preferred.

The very particularly preferred anionic groups here include $-SO_3^-$, $-OSO_3^-$, $-COO^-$, $-PO_3^{2-}$, or $OPO_3^{2-}$. In particular, a sulfonate group $-SO_3^-$ is preferred.

Preferred counterion for anionic groups X is a monovalent cation, in particular $H^+$, an alkali-metal cation or $NR_4^+$, where $R=H$ or C1-C6-alkyl and all R may be identical or different. Especial preference is given to $H^+$, $Na^+$, $K^+$, $Li^+$ and $NH_4^+$, particularly preferably $Na^+$.

A preferred cationic group X can be selected from $-NR^1R^2R^{3+}Z^-$, $-PR^1R^2R^{3+}Z^-$,

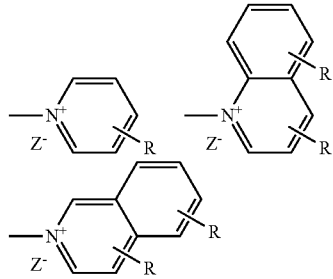

where R stands for H or $C_{1-4}$-alkyl in any desired position, $Z^-$ stands for $Cl^-$, $Br^-$, $I^-$, $CH_3SO_3^-$, $CF_3SO_3^-$, $CH_3PhSO_3^-$, $PhSO_3^-$ $R^1$, $R^2$ and $R^3$ each, independently of one another, stand for H, $C_{1-30}$-alkyl, Ar or $-CH_2Ar$ and Ar stands for an unsubstituted or mono- or polysubstituted aromatic ring or condensed ring systems having 6 to 18 C atoms, in which, in addition, one or two CH groups may be replaced by N.

The preferred cationic groups here include, in particular, $-NR^1R^2R^{3+}Z^-$ and

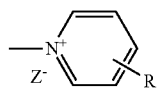

where each one of these groups per se may be preferred.

A preferred nonionic group can be selected from: linear or branched alkyl, where one or more non-adjacent C atoms have been replaced by O, S, and/or N, $-OH$, $-SH$, $-O$-(glycoside)$_o$, $-S$-(glycoside)$_o$, $-OCH_2-CHOH-CH_2-OH$, $-OCH_2Ar(-NCO)_p$, $-OAr(-NCO)_p$, amine oxide,

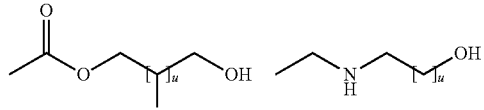

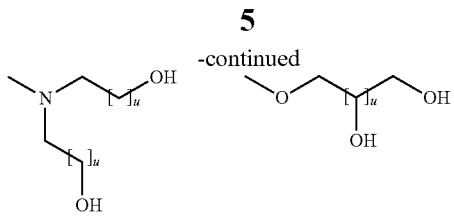

u stands for an integer from the range from 1 to 6, preferably 1 to 4 o' stands for an integer from the range from 1 to 10, p' stands for 1 or 2,

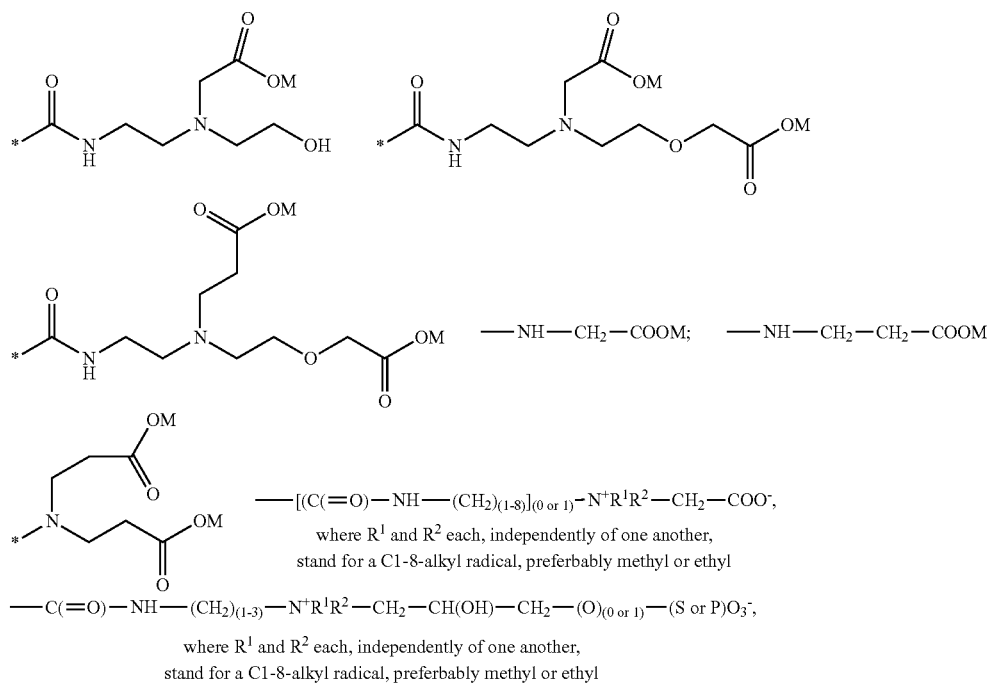

Ar stands for an unsubstituted, mono- or polysubstituted aromatic ring or condensed ring systems having 6 to 18 C atoms, in which, in addition, one or two CH groups may be replaced by C═O and, glycoside stands for an etherified carbohydrate, preferably for a mono- di-, tri- or oligoglucoside.

The preferred nonionic groups here include, in particular, linear or branched alkyl, where one or more non-adjacent C atoms have been replaced by O, S and/or N, —OH and —O-(glycoside)$_{o''}$.

If X=alkyl, where one or more non-adjacent C atoms have been replaced by O, S, and/or N, it is then preferably equal to $R^4$—(B-A)$_{m'''}$— where $R^4$=H or C1-4-alkyl, in particular H or $CH_3$, A=linear or branched alkylene, preferably having 1 to 10 carbon atoms, in particular having 1 to 4 carbon atoms, B═O or S, preferably O, and m''=an integer preferably from the range from 1 to 100, particularly preferably 1 to 30.

The nonionic group X is particularly preferably the group $R^4$—(O—$CH_2CHR^5$)$_{m''}$— where m''=an integer from the range from 1 to 100, preferably 1 to 30, in particular also 1-25, and $R^4$ and $R^5$=H or C1-4-alkyl, in particular H or $CH_3$. $R^4$—(B-A)$_{m'''}$— is particularly preferably a polyethylene glycol or polypropylene glycol unit.

The nonionic group X is particularly preferably the group —CH(OH)—$CH_2$—NH— sach where sach=various sugars and the group —Y—($CH_2$—$CH_2$—O)$_v$—$R^4$ where Y=S, O or NH, preferably O, $R^4$=H or alkyl, preferably H or $CH_3$, and v=1-100, preferably 1-30, in particular also 1-25.

A preferred amphoteric group can be selected from the functional groups of the acetyldiamines, the N-alkylamino acids, the N-alkylaminosulfonic acids, the betaines, the sulfobetaines, or corresponding derivatives, in particular selected from, where M stands for H or an alkali-metal ion, preferably $Li^+$, $Na^+$ or $K^+$:

Particularly preferred compounds according to the invention are those which contain, as hydrophilic group X, one of the preferred anionic groups, the preferred nonionic groups or the preferred zwitterionic groups. Particular preference is given to compounds which contain the groups —$SO_3^-$, —$OSO_3^-$, —$COO^-$, —$PO_3^{2-}$ or $OPO_3^{2-}$, polyethylene glycols or polypropylene glycols, —CH(OH)—$CH_2$—NH-sach, —Y—($CH_2$—$CH_2$—O)$_v$—$R^4$, betaines, or sulfobetaines. Preferred counterions here are $H^+$, $Na^+$, $K^+$ and $NH_4^+$, in particular $Na^+$. Particular preference is given to: —$SO_3^-$, —$COO^-$, polyethylene glycols or polypropylene glycols, sulfobetaines, the group —CH(OH)—$CH_2$—NH-sach and the group —Y—($CH_2$—$CH_2$—O)$_v$—$R^4$. sach here=various sugars and Y=S, O or NH, preferably O, $R^4$=H or alkyl, preferably H or $CH_3$, and v=1-100, preferably 1-30, in particular also 1-25. Compounds where X=—$SO_3^-$ may also be particularly advantageous.

Compounds of the formula (I) in which one or more of the variables have the preferred meanings are particularly advantageous. Compounds of the formula (I) in which all said variables have the preferred meanings, in particular the particularly preferred meanings, are particularly advantageous.

In a variant of the invention, preference is given to compounds of the formula (I) in which the group (spacer-X)

has one of the following meanings: $CR^5(CH_2)_{n''}OH$, $CR^5(CH_2)_{n''}SH$, $CR^5(CH_2)_{n''}COOH$, $CR^5(CH_2)_{n''}SO_3H$, $CR^5(CH_2)_{n''}NH_2$, $CR^5(CH_2)_{n''}NR'_2$, $CR^5(CH_2)_{n''}N^+(CH_3)_3$ $Cl^-$, $CR^5(CH_2)_{n''}NR'_2$—$CH_2$—$COO^-$, $CR^5(CH_2)_{n''}O(CHR^a$—$CHR^bO)_nR''$, $CR^5(CH_2)_{n''}S(CHR^a$—$CHR^bO)_nR''$ or $CR^5(CH_2)_{n''}NH(CHR^a$—$CHR^bO)_nR''$, where n=1-30, preferably=1-25, in particular 4-25, $R^5$, R', R'', $R^a$ and $R^b$ independently of one another=H or alkyl, preferably H or C1-C4 alkyl. $R^5$ is preferably H or $CH_3$, in particular H.

Particular preference is also given to compounds of the formula (I) in which these groups (spacer-X) are present, in particular the preferred group in which n=2-3, preferably=2, x=1, and Rf is equal to $CF_3$—, $CF_3$—$CF_2$— or $CF_3$—$CF_2$—$CF_2$— and Z is equal to:

$R_f$—CHF—$CF_2$—Y—$(CH_2)_m$— or
$R_f$—O—CHF—$CF_2$—Y—$(CH_2)_m$— or
$R_f$—O—$(CF_2)_{1-4}$—CHF—$CF_2$—Y—$(CH_2)_m$— or
$R_f$—O—$(CF_2)_{1-4}$—O—CHF—$CF_2$—Y—$(CH_2)_m$— or
$R_f$—O—$(CF(CF_3)$—$CF_2)_{1-4}$—CHF—$CF_2$—Y—$(CH_2)_m$— or
$R_f$—O—$(CF(CF_3)$—$CF_2)_{1-4}$—O—CHF—$CF_2$—Y—$(CH_2)_m$— or
$R_f$—O—$(CF_2$—O$)_{1-4}$—CHF—$CF_2$—Y—$(CH_2)_m$— or
$R_f$—O—$(CF_2$—$CF_2$—O$)_{1-4}$—CHF—$CF_2$—Y—$(CH_2)_m$— or
$R_f$—O—$(CF_2$—O$)_{1-4}$—$(CF_2$—$CF_2$—O$)_{1-4}$—CHF—$CF_2$—Y—$(CH_2)_m$— where m=0 or 1.

Particular preference is given here to compounds in which Z is equal to:

$R_f$—CHF—$CF_2$—Y—$(CH_2)_m$— or
$R_f$—O—CHF—$CF_2$—Y—$(CH_2)_m$— or
$R_f$—O—$(CF_2)_{1-4}$—CHF—$CF_2$—Y—$(CH_2)_m$— or
$R_f$—O—$(CF_2)_{1-4}$—O—CHF—$CF_2$—Y—$(CH_2)_m$—, in particular compounds where Z=$R_f$—O—CHF—$CF_2$—Y—$(CH_2)_m$— or $R_f$—O—$(CF_2)_{1-4}$—O—CHF—$CF_2$—Y—$(CH_2)_m$—.

Particularly preferred compounds of the invention are compounds of the formulae (IIa) and (IIb):

[F(CF_2)_{n'}(O)_o CHF—CF_2—Y—(CH_2)_m]_2 spacer-X    formula (IIa)

[F(CF_2)_{n'}(O)_o—(CF_2)_{1-4}—O—CHF—CF_2—Y—(CH_2)_m]_2 spacer-X    formula (IIb)

where n'=1-6, preferably 1-3, m=0 or 1, o=0 or 1, preferably 1, Y=O or S, preferably O, and the group (spacer-X)=$CR^5(CH_2)_{n''}OH$, $CR^5(CH_2)_{n''}SH$, $CR^5(CH_2)_{n''}COOH$, $CR^5(CH_2)_{n''}SO_3H$, $CR^5(CH_2)_{n''}NH_2$, $CR^5(CH_2)_{n''}NR'_2$, $CR^5(CH_2)_{n''}N^+(CH_3)_3$ $Cl^-$, $CR^5(CH_2)_{n''}NR'_2$—$CH_2$—$COO^-$, $CR^5(CH_2)_{n''}O(CHR^a$—$CHR^bO)_nR''$, $CR^5(CH_2)_{n''}S(CHR^a$—$CHR^bO)_nR''$ or $CR^5(CH_2)_{n''}NH(CHR^a$—$CHR^bO)_nR''$, where n''=0 or 1, n=1-30, preferably=1-25, in particular 4-25, $R^5$, R', R'', $R^a$ and $R^b$ independently of one another=H or alkyl, preferably H or C1-C4 alkyl. $R^5$ is preferably H or $CH_3$, in particular H.

Particular preference is given to compounds of the formulae (IIa) and (IIb) in which one or more of the variables have the preferred meanings. Compounds of the formulae (IIa) and (IIb) in which all said variables have the preferred meanings are particularly advantageous.

Especial preference is given to compounds of the formulae (III), (III'), (IV) and (IV') in which the variables have the meanings indicated for the formula (I), in particular the preferred meanings:

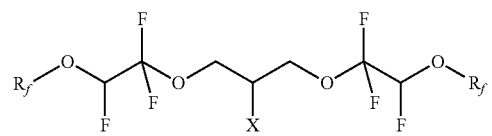

formula (III)

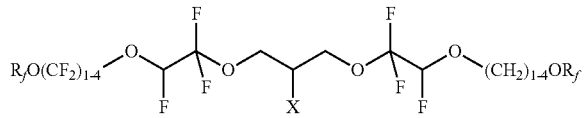

formula (III')

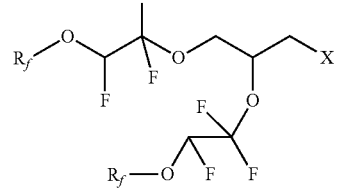

formula (IV)

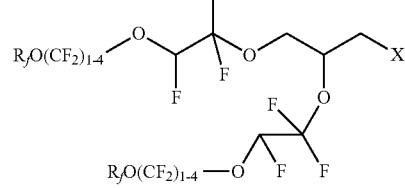

formula (IV')

In a variant of the invention, preference is given to compounds of the formulae (III) and (IV) in which X is a hydrophilic group, as mentioned in the group (spacer-X) in the formulae (IIa) and (IIb), in particular compounds in which Rf is equal to $CF_3$—, $CF_3$—$CF_2$— or $CF_3$—$CF_2$—$CF_2$—.

In a further variant of the invention, preference is given to compounds of the formulae (III') and (IV') in which X is a hydrophilic group, as mentioned in the group (spacer-X) in the formulae (IIa) and (IIb), in particular compounds in which Rf is equal to $CF_3$—, $CF_3$—$CF_2$— or $CF_3$—$CF_2$—$CF_2$—.

Preference is also given to compounds of the formulae (IIIa), (III'a), (IIIb), (III'b), (IVa), (IV'a), (IVb), (IV'b), (IVc) and (IV'c), in which the variables have the meanings indicated for the formulae (I) and (IIa) and (IIb), in particular the preferred meanings, and PEG stands for polyethylene glycol, polypropylene glycol, polyethylene glycol alkyl ether or polypropylene glycol alkyl ether. Alkyl ethers are preferably C1-C4-alkyl ethers, in particular C1-C2-alkyl ethers, especially methyl ether.

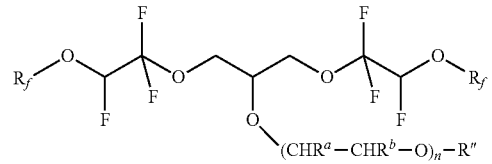

formula (IIIa)

formula (III'a)
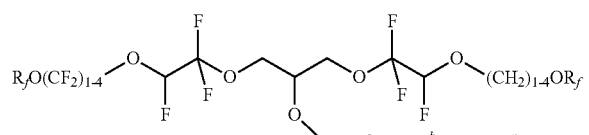
formula (IIIb)
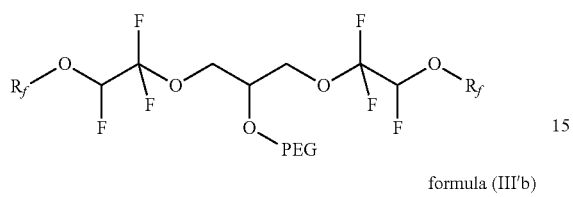
formula (III'b)
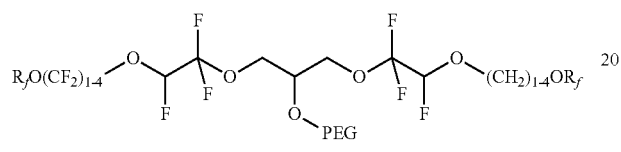
formula (IVa)
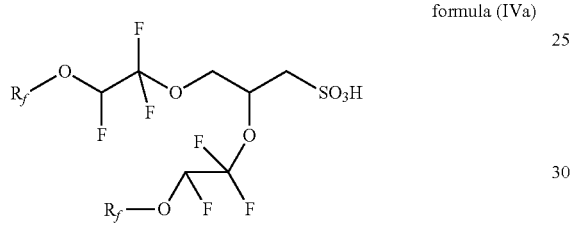
formula (IV'a)
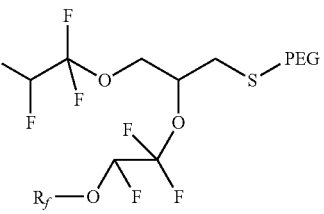 (Note: actual position)
formula (IVc)
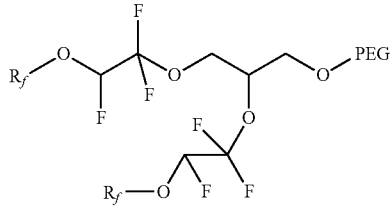
formula (IV'c)
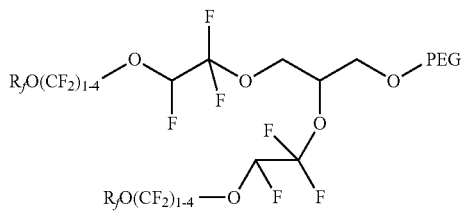
In particular, the following compounds of the formulae (V) to (XII) are particularly preferred:
formula (V)
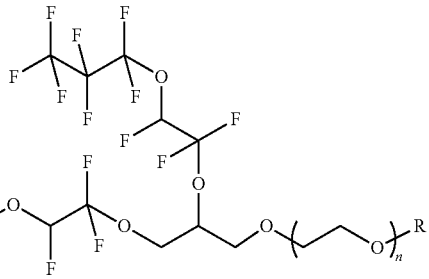
n~6 and R = H or methyl
formula (VI)
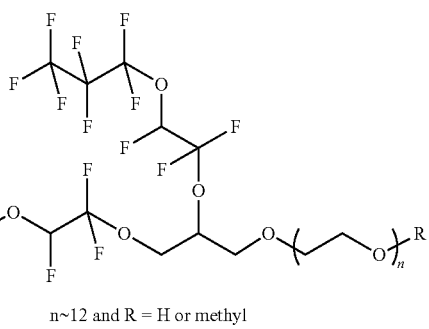
n~12 and R = H or methyl
formula (VII)
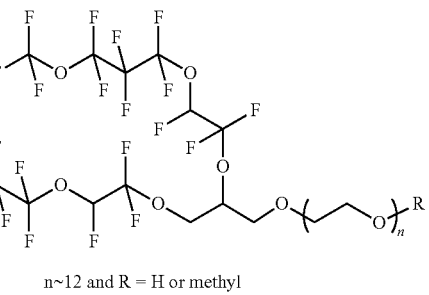
n~12 and R = H or methyl
formula (IVb)
formula (IV'b)

formula (VIII)

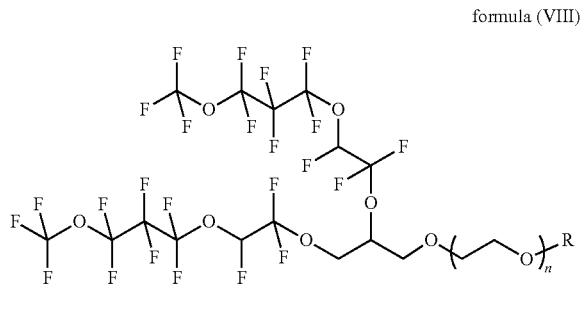

n~24 and R = H or methyl formula (IX)

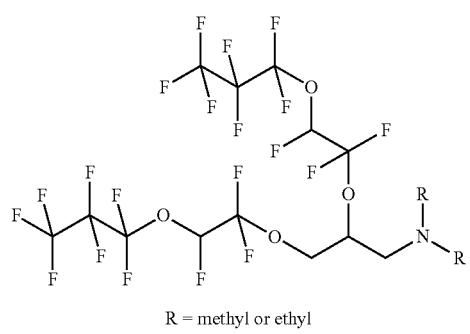

R = methyl or ethyl formula (X)

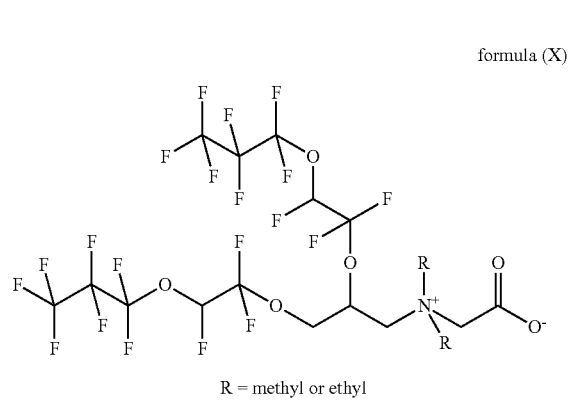

R = methyl or ethyl formula (XI)

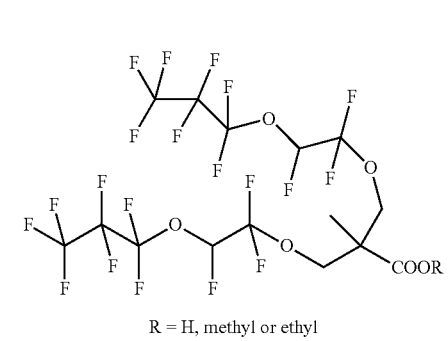

R = H, methyl or ethyl formula (XII)

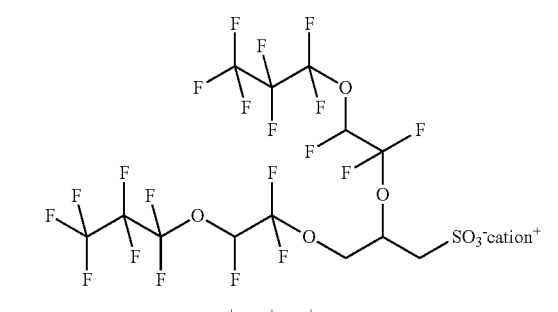

cation$^+$ = H$^+$, Na$^+$, K+ or NH4+

The compounds according to the invention can be prepared by processes known to the person skilled in the art. The following schemes show example syntheses of compounds according to the invention. These processes are generally known to the person skilled in the art and can be carried out under conventional conditions.

The compounds according to the invention, in particular compounds of the formulae (IIa) and (IIb), preferably compounds of the formulae (III), (III'), (IV) and (IV'), can preferably be prepared by the following synthesis routes (shown by way of example for compounds where $R_f$=$C_4F_9$). Particular preference is given here to compounds of the formulae (IIIa), (IIIb), (IVa), (IVb), (IVc), (III'a), (III'b), (IV'a), (IV'b) and (IV'c), in particular of the formulae (V) to (XII).

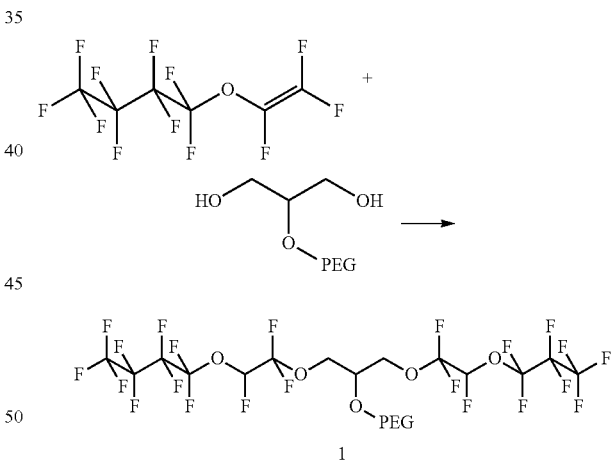

1

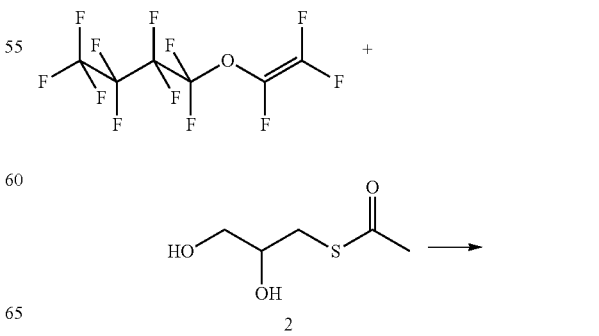

2

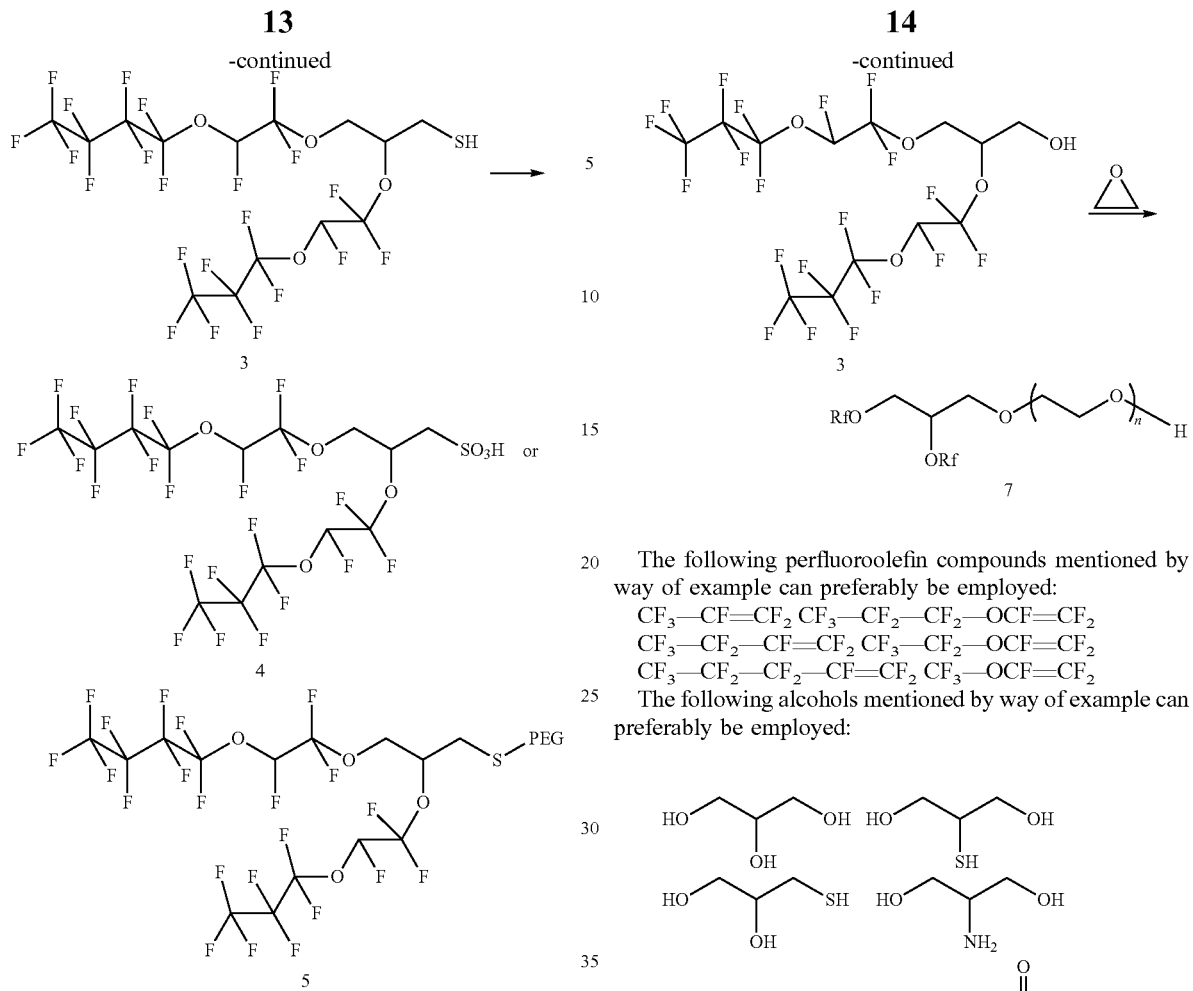

Trifunctional compounds must be protected/activated here so that only two perfluoroolefin molecules are able to react with the molecule. This can be achieved by known protecting groups and corresponding synthesis sequence. Compounds such as 1 can preferably be prepared by reaction of a PEG-ylated glycerol (a glycerol reacted with PEG).

The corresponding thioether 5 is accessible via the protected thioglycerol 2. An intermediate here is compound 3, which can also be converted into the corresponding sulfonate 4 by oxidation.

In the case of the use of serinol, the best starting material is its oxalate salt or the tert-butyloxycarbonyl (BOC)-protected compound.

Compounds such as 7 can preferably be prepared from a monoprotected glycerol 6.

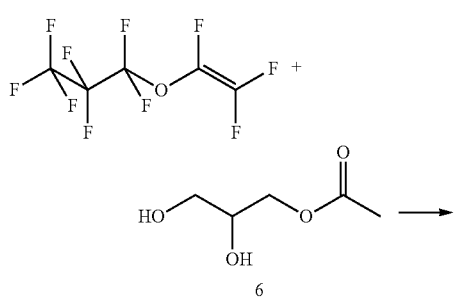

The following perfluoroolefin compounds mentioned by way of example can preferably be employed:

$CF_3-CF=CF_2$ $CF_3-CF_2-CF_2-OCF=CF_2$
$CF_3-CF_2-CF=CF_2$ $CF_3-CF_2-OCF=CF_2$
$CF_3-CF_2-CF_2-CF=CF_2$ $CF_3-OCF=CF_2$

The following alcohols mentioned by way of example can preferably be employed:

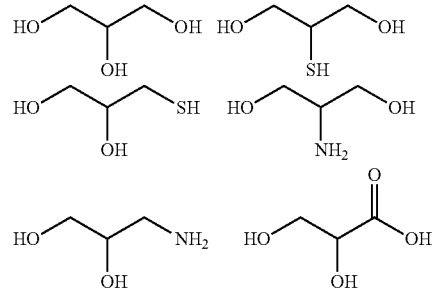

It may be sensible here to protect the selectivity of the individual functional groups:

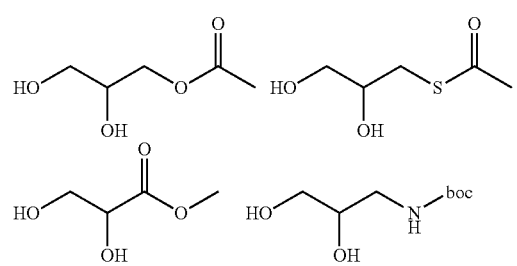

It is advantageous in the case of these compounds that, after the reaction with the perfluoroolefin, the protecting group can easily be removed by boiling in aqueous sodium hydroxide solution or acidification.

The preparation of further compounds according to the invention, in particular further compounds of the formulae (IIa) and (IIb), preferably further compounds of the formulae (III), (III'), (IV) and (IV'), in particular further compounds of the formulae (IIIa), (IIIb), (IVa), (IVb), (IVc), (III'a), (III'b), (IV'a), (IV'b) and (IVc), can be carried out analogously to the illustrative reactions shown above or by other methods known per se to the person skilled in the art from the literature. Particular preference is given here to compounds of the formulae (V) to (XII). The preparation of further compounds according to the invention can also be carried out by other methods known per se to the person skilled in the art from the literature. These methods are generally known to the person skilled in the art and can be carried out under conventional conditions. The alcohols used are commercially available and/or their preparation is familiar to the person skilled in the art.

Advantages of the compounds according to the invention may be, in particular:
- a surface activity which is equal or superior to that of conventional hydrocarbon surfactants with respect to efficiency and/or effectiveness,
- biological and/or abiotic degradability of the substances without the formation of persistent perfluorinated degradation products, such as PFOA (perfluorooctanoic acid) or PFOS (perfluorooctanesulfonate),
- can be prepared by simple processes,
- weak foaming action and/or low foam stabilisation,
- good processability in formulations and/or
- storage stability.

The compounds according to the invention can preferably have a particular surface activity. The compounds of the formula (I) according to the invention, in particular the compounds of the formulae (IIa) and (IIb) and preferably of the formulae (III), (III'), (IV) and (IV'), in particular of the formulae (IIIa), (IIIb), (IVa), (IVb), (IVc), (III'a), (III'b), (IV'a), (IV'b) and (IVc), particularly preferably of the formulae (V)-(XII), may in addition have significantly improved environmental properties compared with the fluorosurfactants of the prior art, since they do not degrade chemically or biologically to give long-chain PFCAs or PFASs.

The compounds according to the invention can preferably be converted completely into mineralisable/regeneratable compounds by corresponding environmental influences.

The degradation of the compounds according to the invention can preferably take place by two mechanisms. In the first step, the carbon skeleton can be degraded by biological activity to the extent that (partially) fluorinated compounds form, which are non-toxic and have a high vapour pressure. Owing to the high volatility, these compounds are able to reach the atmosphere and can be decomposed in the stratosphere by the intense UV radiation prevailing therein to give low-molecular-weight compounds (HF, $COF_2$ etc.). These decomposition products can then be washed out of the atmosphere with rain, transferred into the ground and mineralised therein.

In order to be able to pass through this cycle, it is preferred that the end products are not perfluorinated in the biological decomposition and (stable) salts cannot form.

The invention furthermore relates to a process for the degradation of fluorine-containing compounds comprising the following steps:
a) biological and/or abiotic degradation of the carbon skeleton of the fluorine-containing compounds with formation of, preferably non-toxic, fluorine-containing compounds having a sufficiently high vapour pressure,
b) conversion of the fluorine-containing compounds having a high vapour pressure formed in step a) into a gas phase,
c) degradation of the fluorine-containing compounds having a high vapour pressure formed in step a) to give low-molecular-weight compounds by UV irradiation in the gas phase,
d) conversion of the low-molecular-weight compounds formed in step c) from the gas phase into a liquid and/or solid phase,
e) mineralisation of the low-molecular-weight compounds of the liquid and/or solid phase formed step c).

Preferably, no fluorine-containing, salts are formed in step a).

In particular, no perfluorinated compounds are formed in step a).

Fluorine-containing surfactants are preferably subjected to the degradation process described, in particular surfactants which are based on partially fluorinated.

In the said degradation process, compounds of the formula (I), preferably of the formulae (IIa) and (IIb), in particular of the formulae (III), (III'), (IV) and (IV'), are preferably employed. Particular preference is given here to compounds of the formulae (IIIa), (IIIb), (IVa), (IVb), (IVc), (III'a), (III'b), (IV'a), (IV'b) and (IV'c), in particular those of the formulae (V) to (XII).

The present invention furthermore relates to the use of the compounds according to the invention and the preferred embodiments described above as surface-active agents, for example for improving the flow behaviour and the wetting capacity of coating formulations. Fluorosurfactants of the formulae (IIa) and (IIb), in particular of the formulae (III), (III'), (IV) and (IV'), are preferably used, in particular the said particularly preferred compounds. Preference is given, in particular, to compounds of the formulae (IIIa), (IIIb), (IVa), (IVb), (IVc), (III'a), (III'b), (IV'a), (IV'b) and (IV'c), in particular compounds of the formulae (V) to (XII).

Besides the compounds of the formula (I), in particular the preferred compounds of the formulae (IIa), (IIb), (III), (III'), (IV), (IV'), (IIIa), (IIIb), (IVa), (IVb), (IVc), (III'a), (III'b), (IV'a), (IV'b) and (IV'c), especially of the formulae (V)-(XII), the mixtures according to the invention may also comprise solvents, additives, assistants and fillers as well as non-fluorinated surfactants. Mention may be made by way of example of silicone particles, plasticisers and surface-modified pigments.

Preferred areas of use are, for example, the use of the fluorosurfactants of the formula (I) according to the invention and the preferred compounds of the formulae (IIa), (IIb), (III), (III'), (IV), (IV'), (IIIa), (IIIb), (IVa), (IVb), (IVc), (III'a), (III'b), (IV'a), (IV'b) and (IV'c), especially of the formulae (V)-(XII), as additives in preparations for surface coating, such as paints, coatings, protective coatings, special coatings in electronic or semiconductor applications (for example photoresists, top antireflective coatings, bottom antireflective coatings) or in optical applications (for example photographic coatings, coatings of optical elements), in agrochemicals, in polishes and waxes, for example for furniture, flooring and automobiles, in particular in floor polishes, in fire-extinguishing compositions, lubricants, in photolithographic processes, in particular in immersion photolithography processes, for example in developer solutions, rinse solutions, immersion oils and/or in the photoresists themselves, especially for the production of printed circuits or in additive preparations for addition to corresponding preparations.

In addition, the compounds which can be used in accordance with the invention as surfactant are suitable for washing and cleaning applications, and for use as additives/surfactants in cosmetic products, such as, for example, hair- and body-care products (for example shampoos, hair rinses and hair conditioners), foam baths, creams or lotions having one or more of the following functions: emulsifiers, wetting agents, foaming agents, glidants, antistatic, agents for increasing the resistance to skin greases.

For use, the fluorosurfactants according to the invention are usually introduced into correspondingly designed preparations. Usual use concentrations are 0.01-1.0% by weight of the surfactants according to the invention, based on the preparation as a whole. The present invention likewise relates to corresponding compositions comprising the fluorosurfactants according to the invention. Such compositions preferably comprise a vehicle which is suitable for the respective application, and optionally further active substances and/or optionally assistants. Preferred compositions are paint and coating preparations, fire-extinguishing compositions, lubricants, washing and cleaning compositions and de-icers or developer solutions, rinse solutions, immersion oils and photoresists for photolithographic processes, in particular for immersion photolithography processes and in particular for the production of printed circuits, agrochemicals, floor polishes, cosmetic products, cosmetic products or hydrophobicising compositions for textile finishing or glass treatment. Preferred compositions here are paint and coating preparations and printing inks.

In addition, the present invention also relates to water-based coating formulations which comprise the fluorosurfactants according to the invention, alone or in a mixture with additives. Coating formulations based on the following synthetic film formers are preferably used: polycondensation resins, such as alkyd resins, saturated/unsaturated polyesters, polyamides/imides, silicone resins; phenolic resins; urea resins and melamine resins, polyaddition resins, such as polyurethanes and epoxy resins, polymerisation resins, such as polyolefins, polyvinyl compounds and polyacrylates.

In addition, the fluorosurfactants according to the invention are also suitable for use in coatings based on natural products and modified natural products. Preference is given to coatings based on oils, polysaccharides, such as starch and cellulose, and also based on natural resins, such as cyclic oligoterpenes, polyterpenes and/or shellac.

The fluorosurfactants according to the invention can be used both in physically curing (thermoplastics) and also in crosslinking (elastomers and thermosets) aqueous coating systems. The fluorosurfactants according to the invention preferably improve the flow and wetting properties of the coating systems.

The present invention relates to all uses mentioned here of fluorosurfactants to be employed in accordance with the invention, in particular of the preferred compounds. The respective use of fluorosurfactants for the said purposes is known to the person skilled in the art, meaning that the use of the fluorosurfactants to be employed in accordance with the invention presents no problems.

The complete disclosure content of all applications and publications cited is incorporated into this application by way of reference. For the present invention, both the plural form of a term and also the singular form of a term also means the respective other form, unless expressly indicated otherwise. All features of the present invention can be combined with one another in any way, unless certain features are mutually exclusive. This applies, in particular, to preferred and particularly preferred features. Further features, advantages and variants of the invention also arise from the claims and examples. The following examples explain the present invention in greater detail without restricting the scope of protection.

EXAMPLES

The NMR spectra are measured using a Bruker 400 MHz spectrometer with internal standard.

The IR spectra are measured using a Brucker Alpha Platinum-ATR spectrometer.

Determination of the Static Surface Tension

The static surface tensions γ of aqueous surfactant solutions having various concentrations c (grams per liter) are determined.

Instrument: Dataphysics tensiometer (model DCAT 11)
Temperature of the measurement solutions: 20°±0.2° C.
Measurement method employed: measurement of the surface tension using the Wilhelmy plate method in accordance with DIN EN 14370.
Plate: platinum, length=19.9 mm In the plate method, the surface or interfacial tension of the surfactant solution is calculated from the force acting on the wetted length of a plate, in accordance with the following formula.

$$\gamma = \frac{F}{L \cdot \cos\theta} = \frac{F}{L}$$

γ=interfacial or surface tension; F=force acting on the balance; L=wetted length (19.9 mm); θ=contact angle. The plate consists of roughened platinum and is thus optimally wetted so that the contact angle θ is close to 0°. The term cos θ therefore approximately reaches the value 1, so that only the measured force and the length of the plate have to be taken into account.

Abbreviations
EO ethylene oxide units
THF tetrahydrofuran
MTBE tert-butyl methyl ether
b.p. boiling point
w % percent by weight Example 1: General Ethoxylation Procedure For the ethoxylation, the corresponding alcohol in accordance with the prior art is introduced into a pressure reactor with a catalyst (for example potassium hydroxide) under inert gas, and a corresponding amount of ethylene oxide is condensed in (b.p.: 10.5° C.). The reactor is sealed and heated to 80-150° C. at about 5 bar. After completion of the reaction, the mixture is decompressed and any by-products are removed from the product under reduced pressure.

Example 2

6 EO are adducted onto isopropylideneglycerol (Sigma-Aldrich) as described under Example 1.

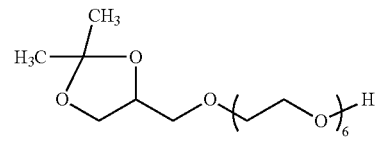

NMR analysis:
$^1$H-NMR (DMSO): 4.13 CH (m), 3.93 CH (dd), 3.7-3.3 ~14 CH$_2$ (m), 1.26 CH$_3$ (s), 1.21 CH$_3$ (s)

$^{13}$C-NMR (DMSO): 108. 8 quart. C; 74.7, 72.8, 72.0, 70.6, 70.2, 66.5, 60.7 sec. C; 27.0, 25.8 prim. C 25 g of this compound are dissolved in 125 ml of THF and initially introduced in a three-necked flask with reflux condenser, thermometer, stirring device and septum. Under a protective-gas atmosphere, 9 g of potassium tert-butoxide (Sigma-Aldrich) are added, during which a slight increase in temperature (to 32° C.) is observed. After 20 min, 10 g of dimethyl sulfate (Sigma-Aldrich) is slowly added. It must be ensured that the temperature does not exceed 37° C. during the addition. After stirring for one hour at room temperature, the reaction mixture is heated to the boiling temperature for 2 hours.

After cooling to room temperature, 50 ml of 10% NH$_3$ solution we added to the batch, which is then stirred for a further 1 hour in order to decompose residual dimethyl sulfate.

20 ml of 2 N HCl are added to the batch (pH=1), and the mixture is warmed under reflux for 6 hours in order to remove the isopropylidene protecting group.

The solvent is removed completely, and the residue is dispersed in 50 ml of acetone.

Salt residues are separated off via a frit, and the solvent is distilled off under reduced pressure.

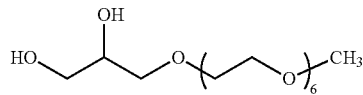

NMR analysis:
$^1$H-NMR (DMSO): 3.8-3.3 ~14 CH$_2$ (m), 3.2 OCH$_3$ (s)

11 g of 1,1,1,2,2,3,3 heptafluoro-3-trifluorovinyloxypropane (ABCR) are added to 5 g of this compound in an autoclave, 10 ml of acetonitrile and 2.4 g of potassium carbonate are mixed and warmed at 80° C. for 66 hours (internal pressure 3.7 bar). 100 ml of water and 100 ml of MTBE are added to the reaction mixture the phases are separated, and the aqueous phase is washed by shaking with 2×50 ml of MTBE. The combined organic phases are washed firstly with 50 ml of water and then with 50 ml of saturated NaCl solution, dried over Na$_2$SO$_4$, and the solvent is separated off under reduced pressure.

The yield is 6 g of a viscous, amber-coloured substance. The following structure arises from the spectroscopic data determined (NMR):

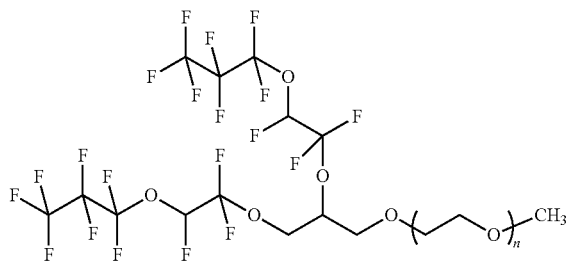

NMR analysis
$^1$H-NMR (DMSO): 5.9 CHF (d), 3.8-3.4 ~14 CH$_2$ (m), 3.3 OCH$_3$ (s)
Static surface tension:
γ 18.9 mN/m (0.1 w %); CMC [g/l] 0.01

Example 3

12 EO are adducted onto isopropylideneglycerol as described under Example 1.

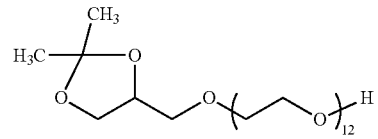

NMR analysis
$^1$H-NMR (DMSO): 4.13 CH (1 m), 3.93 CH (1 dd), 3.7-3.3 CH$_2$ (26, m), 1.26 CH$_3$ (3, s), 1.21 CH$_3$ (3, s)

The further reaction is carried out analogously to Example 2

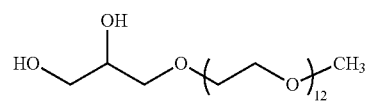

NMR analysis:
$^1$H-NMR (DMSO): 3.8-3.3 CH$_2$ (26, m), 3.2 OCH$_3$ (3, s)

The yield is 7.6 g of a viscous, amber-coloured substance. The following structure arises from the spectroscopic data determined (NMR):

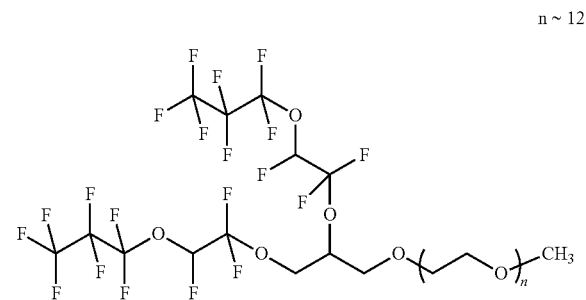

NMR analysis:
$^1$H-NMR (DMSO): 5.9 CHF (2, d), 3.8-3.4 CH (~26, m), 3.3 OCH$_3$ (3, s)
Static surface tension:
γ 18.0 mN/m (0.1 w %)

Example 4

3,700 g of 1,1,2,2,3,3 hexafluoro-1-trifluoromethoxy-3-trifluorovinyloxypropane are warmed in an autoclave with 500 g of glycerol 1-acetate, 670 g of potassium carbonate and 2,300 g of acetonitrile and at 80° C. for 68 hours (internal pressure 2.3 bar).

The batch is washed with water, and the organic phase is separated off. 500 ml of 32% sodium hydroxide solution and 500 ml of water are added to the batch, and the mixture is stirred at the boiling temperature for 72 hours.

The product is extracted with MTBE, washed again with water, dried over Na$_2$SO$_4$ and subjected to fractional distillation in vacuo main fraction (b.p. 82° C. at 0.37 mbar).

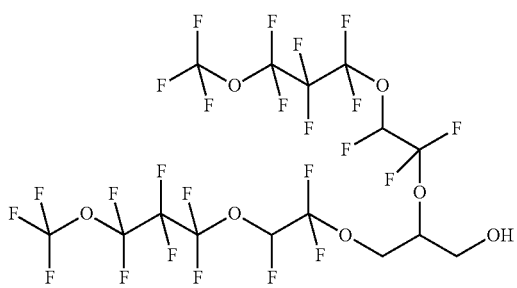 [SMILES: OCC(COC(F)(F)C(F)OC(F)(F)C(F)(F)C(F)(F)OC(F)(F)F)OC(F)(F)C(F)OC(F)(F)C(F)(F)C(F)(F)OC(F)(F)F]

NMR analysis
¹H-NMR (DMSO): 6.6 CHF (2, m), 5.2-3.7 CH (5, m)
The partially fluorinated alcohol is ethoxylated analogously to Example 1 where 12 EO are adducted. The following structure arises from the spectroscopic data determined (NMR:

n ~ 12

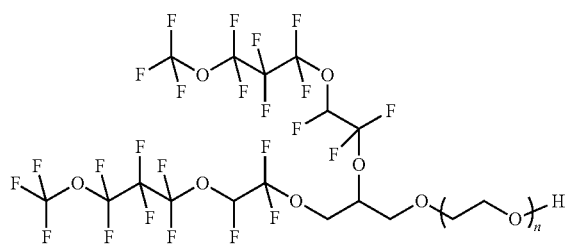

NMR analysis
¹H-NMR (DMSO): 6.8 CHF (2, d), 4.9-4.0 CH (5, m), 3.8-3.2 CH$_2$ CH$_2$O (48, m)
Static surface tension:
γ 18.62 mN/m (0.1 w %)

Example 5

A surfactants having 24 EO units is synthesised analogously to Example 5. The following structure arises from the spectroscopic data determined (NMR):

n ~ 24

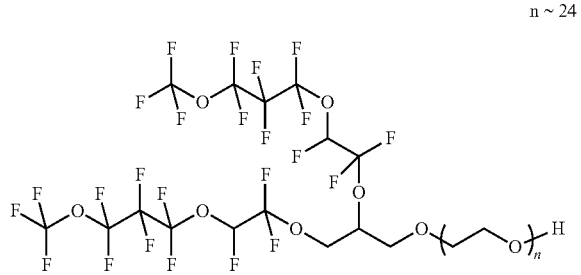

NMR analysis
¹H-NMR (DMSO): 6.8 CHF (2, d), 4.9-4.0 CH (5, m), 3.8-3.2 CH$_2$ CH$_2$O (~96, m)
Static surface tension:
γ 17.58 mN/m (0.1 w %)

Example 6

3.12 g (0.056 mol) of potassium hydroxide are combined with 15 ml of acetonitrile and 2.83 g (0.024 mol) of 3-dimethylaminopropane-1,2-diol (ABCR) in a pressure reactor. 13.90 g (0.052 mol) of 1,1,1,2,2,3,3-heptafluoro-3-trifluorovinyloxypropane are subsequently added. The pressure reactor is sealed, and the mixture is heated to 80° C. Stirring is continued in this reaction for 18 hours.

After completion of the reaction, the reaction mixture is allowed to cool, filtered, and the solvent is removed in vacuo.

For further work-up, the product is subjected to fractional distillation in vacuo, giving 9.66 g (63%) of pale-yellow oil.

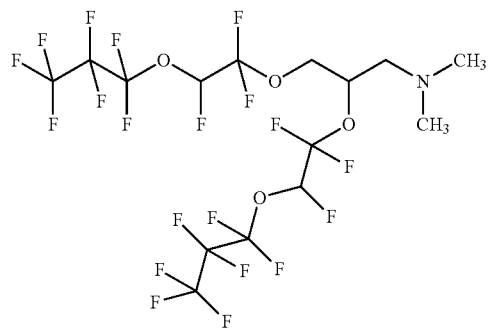 [SMILES: CN(C)CC(COC(F)(F)C(F)OC(F)(F)C(F)(F)C(F)(F)F)OC(F)(F)C(F)OC(F)(F)C(F)(F)C(F)(F)F]

NMR analysis:
¹H-NMR (DMSO): 6.89-6.65 CHF (2, dt), 5.20 CH (1, tt), 4.34-4.16 CH$_2$ (2m), 3.56-3.37 CH$_2$ (2m), 2.88 CH$_3$ (6, s)
7.4 g (0.011 mol) of [2,3-bis-(1,1,2-trifluoro-2-heptafluoropropyloxyethoxy)-propyl]dimethylamine, 1.41 g (0.012 mol) of chloroacetic acid sodium salt (VWR) and 10 ml of 90% ethanol are introduced into a round-bottomed flask and stirred under reflux for 96 h.

The reaction mixture is filtered, and the solvent is removed in vacuo.

The crude product is transferred onto silica gel and separated from the starting material using toluene/ethyl acetate 2/1.

The product is washed off the silica gel using acetone. Yield 4.4 g.

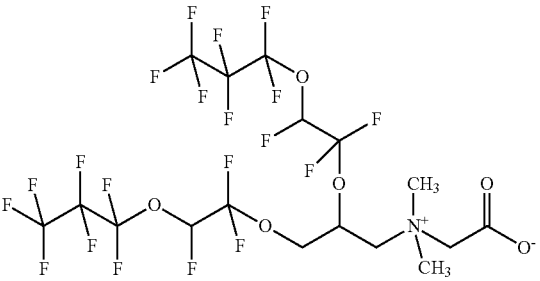 [SMILES: C[N+](C)(CC(=O)[O-])CC(COC(F)(F)C(F)OC(F)(F)C(F)(F)C(F)(F)F)OC(F)(F)C(F)OC(F)(F)C(F)(F)C(F)(F)F]

NMR analysis:
¹H-NMR (DMSO): 6.89-6.65 CHF (2, dd), 5.5 CH (1, s), 4.54-4.16 CH$_2$ (4m), 4.0 CH$_2$ (2, s), 3.40 CH$_3$ (6, ds)
Static surface tension:
15.89 mN/m (1.0 w %)

Example 7

5.0 g (0.034 mol) of methyl 3-hydroxy-2-hydroxymethyl-2-methylpropionate (VWR), 15 ml (0.084 mol) of 1,1,1,2,2,3,3-heptafluoro-3-trifluorovinyloxypropane, 6.1 g (0.044 mol) of potassium carbonate and 25 ml of acetonitrile are combined in a pressure reactor and heated to 80° C. Stirring is continued at this temperature for 48 hours.

The mixture is subsequently allowed to cool, filtered, and the solvent is removed in vacuo.

The crude product is fritted through silica gel, giving 17.1 g (0.025 mol) of methyl 2-methyl-3-(1,1,2-trifluoro-2-heptafluoropropyloxyethoxy)-2-(1,1,2-trifluoro-2-heptafluoropropyloxyethoxymethyl)propionate.

10.00 g (0.015 mol) of methyl 2-methyl-3-(1,1,2-trifluoro-2-heptafluoro-propyloxyethoxy)-2-(1,1,2-trifluoro-2-heptafluoropropyloxyethoxymethyl)-propionate are combined with 1.47 g (0.037 mol) of NaOH in 15 ml (0.257 mol) of ethanol and stirred under reflux for 18 hours.

The solvent is subsequently removed in vacuo, the residue is suspended in acetone and filtered to remove the sodium hydroxide.

The acetone is removed by vacuum distillation, giving 9.4 g (0.014 mol) of the corresponding fluorosurfactant as sodium salt.

Characterisation by IR: COO⁻ st as 1607 cm$^{-1}$
Static surface tension:
16.45 mN/m (1.0 w %)

The invention claimed is:

1. A compound of formula (I)

$$Z_n \text{spacer} X_x \quad (I)$$

where
Z is $R_f$—CHF—CF$_2$—Y—(CH$_2$)$_m$—,
where $R_f$ is CF$_3$—CF$_2$— or CF$_3$—CF$_2$—CF$_2$—, or
Z is
$R_f$—O—CHF—CF$_2$—Y—(CH$_2$)$_m$— or
$R_f$—O—(CF$_2$)$_{1-4}$—CHF—CF$_2$—Y—(CH$_2$)$_m$— or
$R_f$—O—(CF$_2$)$_{1-4}$—O—CHF—CF$_2$—Y—(CH$_2$)$_m$— or
$R_f$—O—(CF(CF$_3$)—CF$_2$)$_{1-4}$—CHF—CF$_2$—Y—(CH$_2$)$_m$— or
$R_f$—O—(CF(CF$_3$)—CF$_2$)$_{1-4}$—O—CHF—CF$_2$—Y—(CH$_2$)$_m$— or
$R_f$—O—(CF$_2$—O)$_{1-4}$—CHF—CF$_2$—Y—(CH$_2$)$_m$— or
$R_f$—O—(CF$_2$—CF$_2$—O)$_{1-4}$—CHF—CF$_2$—Y—(CH$_2$)$_m$— or
$R_f$—O—(CF$_2$—O)$_{1-4}$—(CF$_2$—CF$_2$—O)$_{1-4}$—CHF—CF$_2$—Y—(CH$_2$)$_m$—,
where $R_f$ is CF$_3$— or CF$_3$—CF$_2$— or CF$_3$—CF$_2$—CF$_2$—,
n is 2 or 3,
Y is O or S,
m is 0 or 1,
spacer is a saturated branched or unbranched hydrocarbon unit, optionally containing heteroatoms,
X is —SO$_3^-$, —OSO$_3^-$, —COO⁻, —PO$_3^{2-}$, OPO$_3^{2-}$, —NR$^1$R$^2$R$^{3+}$Z⁻, polyethylene glycol, polypropylene glycol, polyethylene glycol alkyl ether, polypropylene glycol alkyl ether, —CH(OH)—CH$_2$—NH-sach, —Y'—(CH$_2$—CH$_2$—O)$_v$—R$^4$, betaine, sulfo-betaine, —OH, —SH, —O-(glycoside)$_{o'}$, —S-(glycoside)$_{o'}$, —OCH$_2$—CHOH—CH$_2$—OH, —O—CH$_2$Ar(—NCO)$_{p'}$, —OAr(—NCO)$_{p'}$, amine oxide, or one of the following groups and
wherein a counterion for an anionic group X may be present, which is a monovalent cation, H⁺, an alkali-metal cation or NR$_4^+$,
R$^1$, R$^2$ and R$^3$ are H,
Z is Cl⁻, Br⁻, I⁻, CH$_3$SO$_3^-$, CF$_3$SO$_3^-$, CH$_3$PhSO$_3^-$ or PhSO$_3^-$,
R is, each independently H or C$_1$-C$_6$-alkyl,
u is an integer from the range from 1 to 6,
o' is an integer from the range from 1 to 10,
p' is 1 or 2,
Ar is an unsubstituted, mono- or polysubstituted aromatic ring or condensed ring system having 6 to 18 C atoms, in which one or two CH groups are optionally replaced by C=O,
glycoside is an etherified carbohydrate,
sach is a sugar,
Y' is S, O or NH,
R$^4$ is H or alkyl,
v is 1-100, and
x is 1,
where all indices are selected so that no —O—O— bonds are present, 2. The compound according to claim 1, wherein
spacer is a saturated, branched or linear hydrocarbon unit, and Z is
R$_f$—O—CHF—CF$_2$—Y—(CH$_2$)$_m$— or
R$_f$—O—(CF$_2$)$_{1-4}$—CHF—CF$_2$—Y—(CH$_2$)$_m$— or
R$_f$—O—(CF$_2$)$_{1-4}$—O—CHF—CF$_2$—Y—(CH$_2$)$_m$— or
R$_f$—O—(CF(CF$_3$)—CF$_2$)$_{1-4}$—CHF—CF$_2$—Y—(CH$_2$)$_m$— or
R$_f$—O—(CF(CF$_3$)—CF$_2$)$_{1-4}$—O—CHF—CF$_2$—Y—(CH$_2$)$_m$— or
R$_f$—O—(CF$_2$—O)$_{1-4}$—CHF—CF$_2$—Y—(CH$_2$)$_m$— or
R$_f$—O—(CF$_2$—CF$_2$—O)$_{1-4}$—CHF—CF$_2$—(CH$_2$)$_m$— or
R$_f$—O—(CF$_2$—O)$_{1-4}$—(CF$_2$—CF$_2$—O)$_{1-4}$—CHF—CF$_2$—Y—(CH$_2$)$_m$—.

3. The compound according to claim 1, wherein Z is
R$_f$—O—CHF—CF$_2$—Y—(CH$_2$)$_m$— or
R$_f$—O—(CF$_2$)$_{1-4}$—CHF—CF$_2$—Y—(CH$_2$)$_m$— or
R$_f$—O—(CF$_2$)$_{1-4}$—O—CHF—CF$_2$—Y—(CH$_2$)$_m$—.

4. The compound according to claim 1, wherein Z is R$_f$O—CHF—CF$_2$—Y—(CH$_2$)$_m$— or R$_f$—O—(CF$_2$)$_{1-4}$—O—CHF—CF$_2$—Y—(CH$_2$)$_m$—.

5. The compound according to claim 1, wherein R$_f$ is CF$_3$— or CF$_3$—CF$_2$—CF$_2$—,
provided that, if Z is R$_f$—CHF—CF$_2$—Y—(CH$_2$)$_m$—, then R$_f$ is CF$_3$—CF$_2$—CF$_2$—.

6. The compound according to claim 1, wherein
spacer-X is CR$^5$(CH$_2$)$_{n''}$OH, CR$^5$(CH$_2$)$_{n''}$SH, CR$^5$(CH$_2$)$_{n''}$COOH, CR$^5$(CH$_2$)$_{n''}$SO$_3$H, CR$^5$(CH$_2$)$_{n''}$NH$_2$, CR$^5$(CH$_2$)$_{n''}$NR'$_2$, CR$^5$(CH$_2$)$_{n''}$—N$^+$(CH$_3$)$_3$ Cl$^-$, CR$^5$(CH$_2$)$_{n''}$NR'$_2$—CH$_2$—COO$^-$, CR$^5$(CH$_2$)$_{n''}$O(CHR$^a$—CHR$^b$O)$_{n'''}$R'', CR$^5$(CH$_2$)$_{n''}$S(CHR$^a$—CHR$^b$O)$_{n'''}$R'' or CR$^5$(CH$_2$)$_{n''}$NH(CHR$^a$—CHR$^b$O)$_{n'''}$R'',
n'' is 0 or 1,
n''' is 1-30,
n is 2,
R$^5$, R' and R'' independently of one another are H or alkyl, and
R$^a$ and R$^b$ are H.

7. A compound, which is of formula (IIa) or (IIb):

[F(CF$_2$)$_{n'}$(O)$_o$CHF—CF$_2$—Y—(CH$_2$)$_m$]$_2$spacer-X     formula (IIa)

[F(CF$_2$)$_{n'}$(O)$_o$—(CF$_2$)$_{1-4}$—O—CHF—CF$_2$—Y—(CH$_2$)$_m$]$_2$spacer-X     formula (IIb)

where
n' is 1-6, provided that, if the compound is of the formula (IIa) and o is 0, then n' is not 1,
m is 0 or 1,
o is 0 or 1,
Y is O or S,
spacer-X is —CR$^5$(CH$_2$)$_{n''}$OH, CR$^5$(CH$_2$)$_{n''}$SH, CR$^5$(CH$_2$)$_{n''}$COOH, CR$^5$(CH$_2$)$_{n''}$SO$_3$H, CR$^5$(CH$_2$)$_{n''}$NH$_2$, CR$^5$(CH$_2$)$_{n''}$NR'$_2$, CR$^5$(CH$_2$)$_{n''}$N$^+$(CH$_3$)$_3$ Cl$^-$, CR$^5$(CH$_2$)$_{n''}$NR'$_2$—CH$_2$—COO$^-$, CR$^5$(CH$_2$)$_{n''}$O(CHR$^a$—CHR$^b$O)$_{n'''}$R'', CR$^5$(CH$_2$)$_{n''}$S(CHR$^a$—CHR$^b$O)$_{n'''}$R'' or CR$^5$(CH$_2$)$_{n''}$NH(CHR$^a$—CHR$^b$O)$_{n'''}$R'',
n'' is 0 or 1,
n''' is 1-30, and
R$^5$, R' and R'' independently of one another are H or alkyl, and
R$^a$ and R$^b$ are H or alkyl.

8. The compound according to claim 7, wherein, o is 1 and Y is O.

9. The compound according to claim 1, which is of formula (III), (III'), (IV) or (IV'):

formula (III)

formula (III')

formula (IV)

formula (IV')

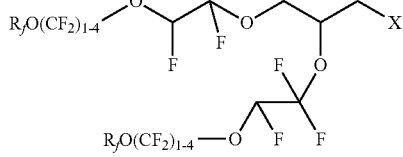

where
R$_f$ is CF$_3$— or CF$_3$—CF$_2$— or CF$_3$—CF$_2$—CF$_2$—, and
X is —SO$_3$-, —OSO$_3^-$, —COO$^-$, —PO$_3^{2-}$, OPO$_3^{2-}$, polyethylene glycol, polypropylene glycol, polyethylene glycol alkyl ether, polypropylene glycol alkyl ether, —CH(OH)—CH$_2$—NH-sach, —Y'—(CH$_2$—CH$_2$—O)$_v$—R$^4$, betaine, or sulfo-betaine.

10. The compound according to claim 1, which is of formula (IIIa), (III'a), (IIIb), (III'b), (IVa), (IV'a), (IVb), (IV'b), (IVc) or (IV'c):

formula (IIIa)

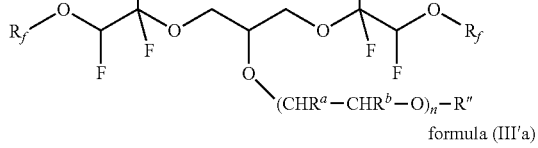
formula (III'a)

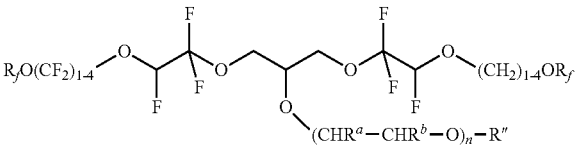
formula (IIIb)

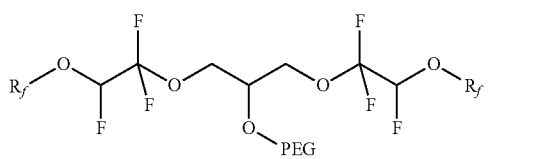

formula (III'b)
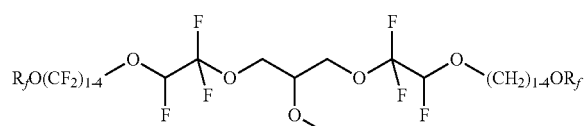

formula (IVa)
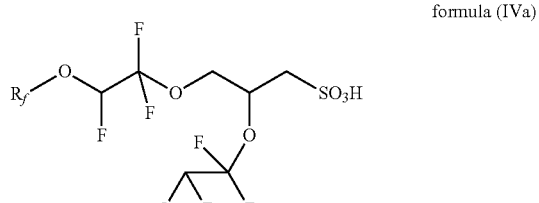

formula (IV'a)
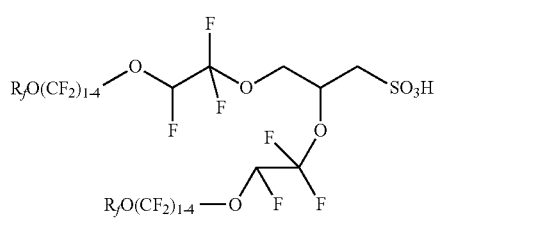

formula (IVb)
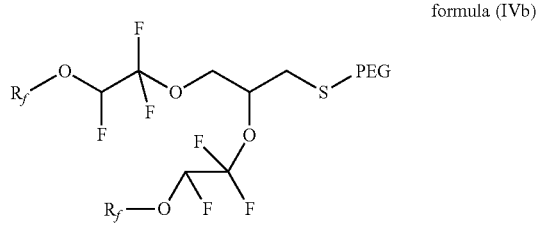

formula (IV'b)
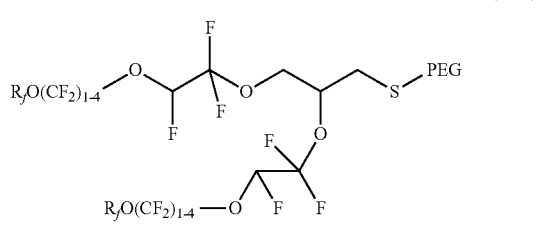

formula (IVc)
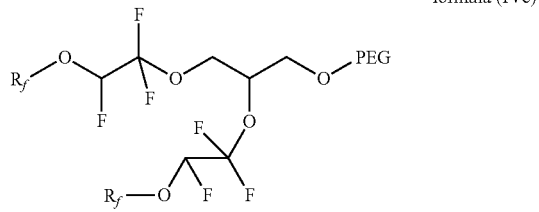

formula (IV'c)
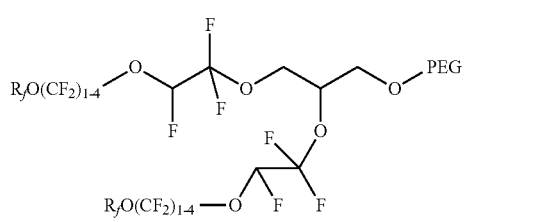

where
$R^a$ and $R^b$ are H,
n''' is 1-30,
R'' is H or alkyl,
$R_f$ is $CF_3$— or $CF_3$—$CF_2$— or $CF_3$—$CF_2$—$CF_2$—, and
PEG stands for polyethylene glycol, polypropylene glycol, polyethylene glycol alkyl ether or polypropylene glycol alkyl ether.

11. A compound, which is of formula (V), (VI), (VII), (VIII), (IX), (X), (XI) or (XII):

formula (V)
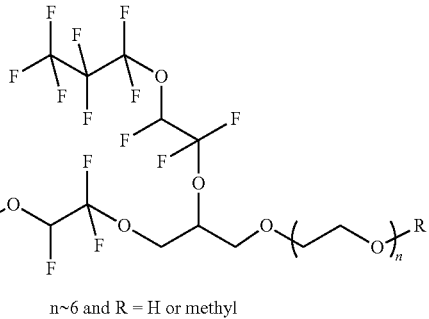

n~6 and R = H or methyl formula (VI)
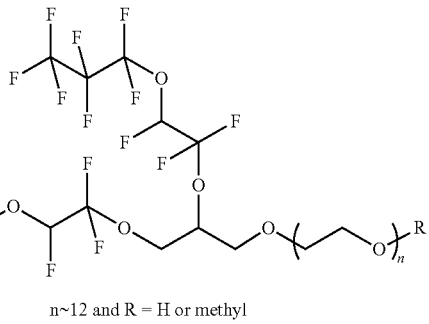

n~12 and R = H or methyl formula (VII)
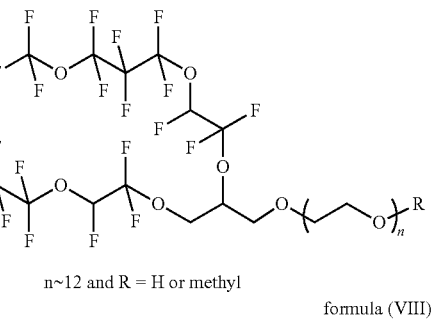

n~12 and R = H or methyl formula (VIII)
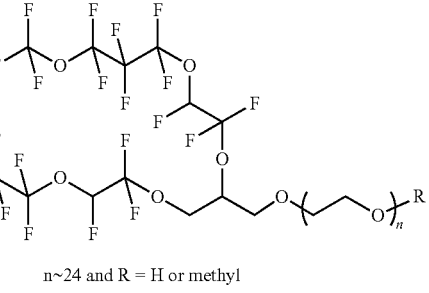

n~24 and R = H or methyl

-continued

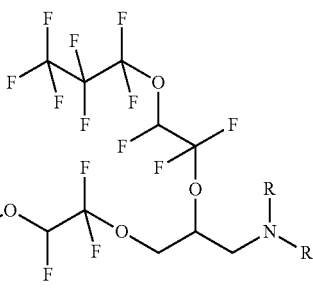

R = methyl or ethyl formula (IX)

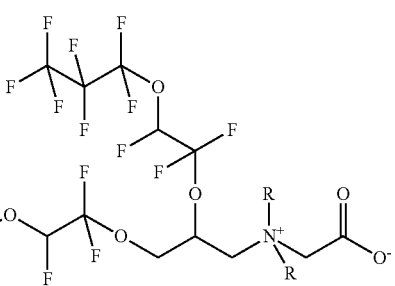

R = methyl or ethyl formula (X)

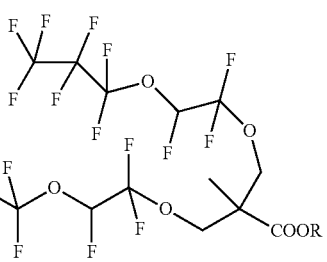

R = H, methyl or ethyl formula (XI)

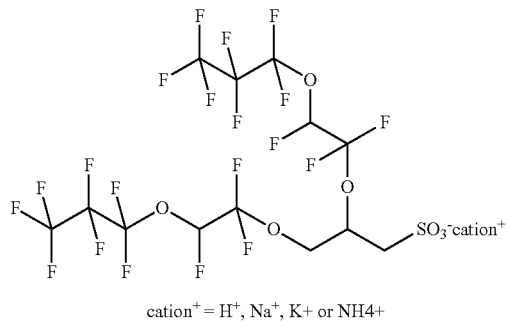

cation$^+$ = H$^+$, Na$^+$, K+ or NH4+ formula (XII)

12. The compound according to claim 1, wherein
spacer-X is CR$^5$(CH$_2$)$_{n''}$OH, CR$^5$(CH$_2$)$_{n''}$SH, CR$^5$(CH$_2$)$_{n''}$COOH, CR$^5$(CH$_2$)$_{n''}$SO$_3$H, CR$^5$(CH$_2$)$_{n''}$NH$_2$, CR$^5$(CH$_2$)$_{n''}$NR'$_2$, CR$^5$(CH$_2$)$_{n''}$NR'$_2$—CH$_2$—COO$^-$, CR$^5$(CH$_2$)$_{n''}$O(CHR$^a$—CHR$^b$O)$_{n'''}$R'', CR$^5$(CH$_2$)$_{n''}$S(CHR$^a$—CHR$^b$O)$_{n'''}$R'' or CR$^5$(CH$_2$)$_{n''}$NH(CHR$^a$—CHR$^b$O)$_{n'''}$R'',
n'' is 0 or 1,
n''' is 1-30,
R$^5$, R' and R'' independently of one another are H or alkyl, and
R$^a$ and R$^b$ are H.

13. The compound according to claim 1, wherein X is amine oxide.

14. A composition comprising a compound according to claim 1 and a vehicle and optionally further active substances.

15. The composition according to claim 14, which is selected from the group consisting of paints, coating preparations, fire-extinguishing compositions, lubricants, washing compositions, cleaning compositions, de-icers, developer solutions, wash solutions, photoresists for photolithographic processes, cosmetic products, agrochemicals, floor polishes, hydrophobicising compositions for textile finishing, and hydrophobicising compositions for glass treatment.

16. The composition according to claim 14, which is selected from the group consisting of paints, coatings, printing inks, protective coatings, special coatings in electronic or optical applications, photoresists, top antireflective coatings, bottom antireflective coatings, developer solutions, wash solutions, photoresists for photolithographic processes, cosmetic products, agrochemicals, floor polishes, photographic coatings, and coatings of optical elements.

17. A composition comprising a compound according to claim 7 and a vehicle and optionally further active substances.

18. The composition according to claim 17, which is selected from the group consisting of paints, coating preparations, fire-extinguishing compositions, lubricants, washing compositions, cleaning compositions, de-icers, developer solutions, wash solutions, photoresists for photolithographic processes, cosmetic products, agrochemicals, floor polishes, hydrophobicising compositions for textile finishing, and hydrophobicising compositions for glass treatment.

19. The composition according to claim 17, which is selected from the group consisting of paints, coatings, printing inks, protective coatings, special coatings in electronic or optical applications, photoresists, top antireflective coatings, bottom antireflective coatings, developer solutions, wash solutions, photoresists for photolithographic processes, cosmetic products, agrochemicals, floor polishes, photographic coatings, and coatings of optical elements.

20. A compound of formula (I)

$$Z_n\text{spacer}X_x \qquad (I)$$

where
Z is R$_f$—CHF—CF$_2$—Y—(CH$_2$)$_m$—,
  where R$_f$ is CF$_3$—CF$_2$— or CF$_3$—CF$_2$—CF$_2$—, or
Z is
  R$_f$—O—CHF—CF$_2$—Y—(CH$_2$)$_m$— or
  R$_f$—O—(CF$_2$)$_{1-4}$—CHF—CF$_2$—Y—(CH$_2$)$_m$— or
  R$_f$—O—(CF$_2$)$_{1-4}$—O—CHF—CF$_2$—Y—(CH$_2$)$_m$— or
  R$_f$—O—(CF(CF$_3$)—CF$_2$)$_{1-4}$—CHF—CF$_2$—Y—(CH$_2$)$_m$— or
  R$_f$—O—(CF(CF$_3$)—CF$_2$)$_{1-4}$—O—CHF—CF$_2$—Y—(CH$_2$)$_m$— or
  R$_f$—O—(CF$_2$—O)$_{1-4}$—CHF—CF$_2$—Y—(CH$_2$)$_m$— or
  R$_f$—O—(CF$_2$—CF$_2$—O)$_{1-4}$—CHF—CF$_2$—Y—(CH$_2$)$_m$— or
  R$_f$—O—(CF$_2$—O)$_{1-4}$—(CF$_2$—CF$_2$—O)$_{1-4}$—CHF—CF$_2$—Y—(CH$_2$)$_m$—,
  where R$_f$ is CF$_3$— or CF$_3$—CF$_2$— or CF$_3$-CF$_2$-CF$_2$-,
n is 2 or 3,
Y is O or S,
m is 0 or 1,
spacer is a saturated branched or unbranched hydrocarbon unit, optionally containing heteroatoms, X is $-SO_3^-$, $-OSO_3^-$, $-COO^-$, $-PO_3^{2-}$, $OPO_3^{2-}$, polyethylene glycol, polypropylene glycol, polyethylene glycol alkyl ether, polypropylene glycol alkyl ether, $-CH(OH)-CH_2-NH$-sach, $-Y'-(CH_2-CH_2-O)_v-R^4$, betaine or sulfo-betaine, sach is a sugar, Y' is S, O or NH, $R^4$ is H or alkyl, v is 1-100, and x is 1, where all indices are selected so that no $-O-O-$ bonds are present.

21. The compound according to claim 20, which is of formula (III), (III'), (IV) or (IV'):

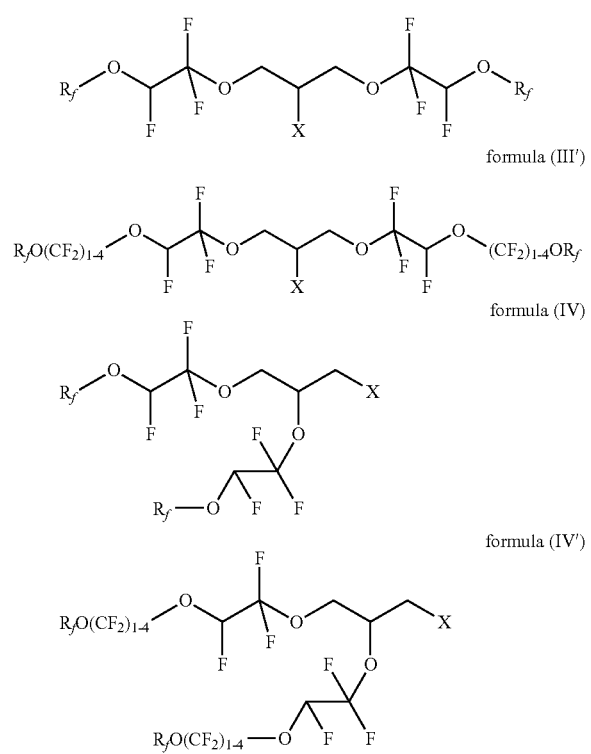

formula (III)

formula (III')

formula (IV)

formula (IV')

wherein $R_f$ is $CF_3-$ or $CF_3-CF_2-$ or $CF_3-CF_2-CF_2-$ and

X is $-SO_3^-$, $-OSO_3^-$, $-COO^-$, $-PO_3^{2-}$, $OPO_3^{2-}$, polyethylene glycol, polypropylene glycol, polyethylene glycol alkyl ether, polypropylene glycol alkyl ether, $-CH(OH)-CH_2-NH$-sach, $-Y'-(CH_2-CH_2-O)_v-R^4$, betaine or sulfo-betaine.

22. A compound of formula (I)

$$Z_n \text{spacer} X_x \qquad (I)$$

where

Z is $R_f-CHF-CF_2-Y-(CH_2)_m-$, where $R_f$ is $CF_3-CF_2-$ or $CF_3-CF_2-CF_2-$, or Z is $R_f-O-CHF-CF_2-Y-(CH_2)_m-$ or $R_f-O-(CF_2)_{1-4}-CHF-CF_2-Y-(CH_2)_m-$ or $R_f-O-(CF_2)_{1-4}-O-CHF-CF_2-Y-(CH_2)_m-$ or $R_f-O-(CF(CF_3)-CF_2)_{1-4}-CHF-CF_2-Y-(CH_2)_m-$ or $R_f-O-(CF(CF_3)-CF_2)_{1-4}-O-CHF-CF_2-Y-(CH_2)_m-$ or $R_f-O-(CF_2-O)_{1-4}-CHF-CF_2-Y-(CH_2)_m-$ or $R_f-O-(CF_2-CF_2-O)_{1-4}-CHF-CF_2-Y-(CH_2)_m-$ or $R_f-O-(CF_2-O)_{1-4}-(CF_2-CF_2-O)_{1-4}-CHF-CF_2-Y-(CH_2)_m-$, where $R_f$ is $CF_3-$ or $CF_3-CF_2-$ or $CF_3-CF_2-CF_2-$, n is 2 or 3, Y is O or S, m is 0 or 1, spacer-X is $CR^5(CH_2)_{n''}O(CHR^a-CHR^bO)_{n'''}R''$, $CR^5(CH_2)_{n''}S(CHR^a-CHR^bO)_{n'''}R''$ or $CR^5(CH_2)_{n''}NH(CHR^a-CHR^bO)_{n'''}R''$, n" is 0 or 1, n'" is 1-30, $R^5$ and R" independently of one another are H or alkyl, and $R^a$ and $R^b$ are H, sach is a sugar, Y' is S, O or NH, $R^4$ is H or alkyl, v is 1-100, and x is 1, where all indices are selected so that no $-O-O-$ bonds are present.

* * * * *